(12) United States Patent
Servidio et al.

(10) Patent No.: US 8,926,708 B2
(45) Date of Patent: Jan. 6, 2015

(54) STEM WITH PRESSFIT POROUS ELEMENT

(71) Applicant: Howmedica Osteonics Corp., Mahwah, NJ (US)

(72) Inventors: Damon J. Servidio, Towaco, NJ (US); G. Douglas Letson, Tampa, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 13/966,989

(22) Filed: Aug. 14, 2013

(65) Prior Publication Data

US 2013/0326859 A1    Dec. 12, 2013

Related U.S. Application Data

(62) Division of application No. 12/909,240, filed on Oct. 21, 2010, now Pat. No. 8,535,386.

(51) Int. Cl.
*A61F 2/30* (2006.01)
*A61F 2/36* (2006.01)
*A61F 2/38* (2006.01)

(52) U.S. Cl.
CPC ............. *A61F 2/30* (2013.01); *A61F 2/30734* (2013.01); *A61F 2/30767* (2013.01); *A61F 2/3662* (2013.01); *A61F 2/3859* (2013.01); *A61F 2/389* (2013.01); *A61F 2002/30013* (2013.01); *A61F 2002/30332* (2013.01); *A61F 2002/30354* (2013.01); *A61F 2002/30604* (2013.01); *A61F 2002/30736* (2013.01); *A61F 2002/30738* (2013.01); *A61F 2002/3092* (2013.01)
USPC .............. 623/23.28; 623/23.23; 623/23.46; 623/23.52; 623/23.55; 623/20.36

(58) Field of Classification Search
CPC ........ A61F 2/367; A61F 2/389; A61F 2/3662; A61F 2002/3662; A61F 2/30724; A61F 2/30734; A61F 2/30767; A61F 2002/30724; A61F 2002/30734; A61F 2002/30736; A61F 2002/30738; A61F 2002/3631; A61F 2002/30013
USPC .................. 623/23, 23.3, 23.36, 23.46, 23.52, 623/23.55, 23.23
See application file for complete search history.

(56) References Cited

U.S. PATENT DOCUMENTS

| | | |
|---|---|---|
| 4,549,319 A | 10/1985 | Meyer |
| 4,944,759 A | 7/1990 | Mallory et al. |
| 5,057,101 A | 10/1991 | Dorr et al. |
| 5,108,435 A | 4/1992 | Gustavson et al. |
| 5,192,324 A | 3/1993 | Kenna |
| 5,653,765 A | 8/1997 | McTighe et al. |
| 5,989,472 A | 11/1999 | Ashby et al. |
| 6,156,070 A | 12/2000 | Incavo et al. |
| 6,209,621 B1 | 4/2001 | Treacy |

(Continued)

*Primary Examiner* — David H Willse
*Assistant Examiner* — Javier Blanco
(74) *Attorney, Agent, or Firm* — Lerner, David, Littenberg, Krumholz & Mentlik, LLP

(57) ABSTRACT

An implant assembly comprises a stem and an augment. The augment includes a porous outer region which is integrally formed onto a solid inner region. The augment further includes, solid posts integrally formed on the solid inner region and extend through the porous outer region to the outer surface of the augment. The posts are integrally formed with and surrounded by the porous region and are designed to allow assembly of the augment to the stem without damaging the structure of the porous region. A method of attaching the augment is described, wherein a tool is designed to grip to posts of the augment and apply loads through these posts during assembly.

5 Claims, 5 Drawing Sheets

(56) References Cited

U.S. PATENT DOCUMENTS

| | | |
|---|---|---|
| 6,494,883 B1 | 12/2002 | Ferree |
| 6,616,698 B2 | 9/2003 | Scarborough |
| 6,656,226 B2 | 12/2003 | Yoon |
| 6,866,683 B2 | 3/2005 | Gerbec et al. |
| 6,887,276 B2 | 5/2005 | Gerbec et al. |
| 6,981,991 B2 | 1/2006 | Ferree |
| 7,192,448 B2 | 3/2007 | Ferree |
| 7,291,174 B2 | 11/2007 | German et al. |
| 7,507,256 B2 | 3/2009 | Heck et al. |
| 7,537,664 B2 | 5/2009 | O'Neill et al. |
| 7,578,851 B2 | 8/2009 | Dong et al. |
| 7,691,149 B2 | 4/2010 | Brown et al. |
| 2005/0107883 A1 | 5/2005 | Goodfried et al. |
| 2006/0147332 A1 | 7/2006 | Jones et al. |
| 2007/0142914 A1 | 6/2007 | Jones et al. |
| 2008/0167722 A1 | 7/2008 | Metzger et al. |
| 2009/0011384 A1 | 1/2009 | Collins et al. |
| 2010/0003638 A1 | 1/2010 | Collins et al. |
| 2010/0003640 A1 | 1/2010 | Damstra et al. |
| 2010/0016980 A1 | 1/2010 | Donno et al. |
| 2010/0076565 A1 | 3/2010 | Thomas |
| 2010/0100190 A1 | 4/2010 | May et al. |
| 2010/0100191 A1 | 4/2010 | May et al. |
| 2010/0114323 A1 | 5/2010 | Deruntz et al. |

STEM WITH PRESSFIT POROUS ELEMENT

CROSS-REFERENCE TO RELATED APPLICATION

The present application is a divisional of U.S. patent application Ser. No. 12/909,240, filed on Oct. 21, 2010, now U.S. Pat. No. 8,535,386, the disclosure of which is incorporated herein by reference.

BACKGROUND OF THE INVENTION

This invention relates to a method for attaching a porous augment to an orthopedic implant.

Orthopedic implant systems are available for joint replacement surgeries of the hip, knee, shoulder and other articular joints. Orthopedic implants are also available for non-articulating orthopedic applications, which may include trauma and intercalary surgeries. Overall, these implant systems may include articulating resurfacing components, segmental elements, stems, offsets and augments. First generation orthopedic stem implants were monolithic, manufactured from cobalt chrome or titanium materials, and configured with either a round or square longitudinal stem element. The first generation orthopedic implants utilized bone cement for fixation within the body.

Later generations of implant designs introduced porous ingrowth surface technology. An example of this porous ingrowth surface technology is described in U.S. Pat. No. 5,192,324. Briefly, this patent describes a porous coating for bone ingrowth or interlocking with bone cement. Orthopedic systems with porous ingrowth technology provide clinical benefits including improved soft tissue fixation, integration and stability.

As technology continues to evolve, porous ingrowth surfaces are manufactured from advanced machining techniques such as the laser produced porous structure described in U.S. Pat. No. 7,537,664 and the laser produced porous surface describe in U.S. Patent Application 2006/0147332, the disclosures of which are incorporated herein by reference.

A challenge with the advanced porous ingrowth surface, such as the laser produced porous surface, is the ability to assemble the augment, stem or any segmental implants without damaging the ingrowth surface. Therefore, a need exists for implants with structural configurations specifically designed to allow for assembly of implant components without while preserving the integrity of the porous ingrowth surface.

BRIEF SUMMARY OF THE INVENTION

One aspect of the invention is an implant comprising a first part and a second part. The first part is a bone implant, such as a stem, for insertion into the intramedullary canal of a long bone, which has an outer surface. The second part has a non-porous body having a central axis, an inner surface and an outer surface. The inner surface extends circumferentially about the central axis and receives the first part outer surface. A porous structure has an inner surface and is integrally formed on at least a portion of the non-porous body outer surface and has a tissue contacting outer surface. A plurality of non-porous posts are integrally formed on the non-porous body outer surface. The axis of at least one post is oriented perpendicular to the non-porous body central axis. The post has a first outer surface extending parallel to the outer post axis and completely surrounded by the porous structure. The post has a second outer surface extends perpendicular to the post axis and is located at or below the porous structure outer surface.

Alternate aspects of the of the implant may include any of, or any combination of the following features: the posts have a circular cross section; there are three posts that may extend perpendicular to the non-porous body central axis; at least one post extends in a non-perpendicular direction to the non-porous body central axis; a non-porous body comprising a constant diameter region and an inwardly tapering region wherein there is at least one post within the constant diameter region and at least one post in the tapered region; the post within the constant diameter region is oriented perpendicular to the central axis and the post within the tapered region is oriented non-perpendicular or parallel to the central axis.

Another aspect of the invention is an implant comprising a non-porous body having a central axis, an inner surface and an outer surface. The inner surface extends circumferentially about the central axis. A porous structure has an inner surface integrally formed on at least a portion of the non-porous body outer surface and has a tissue contacting outer surface. A plurality of non-porous posts may be integrally formed on the non-porous body. The posts have side surfaces and an outer surface. At least one post is oriented perpendicular to the non-porous body central axis and at least one post is oriented non-perpendicular to the non-porous body central axis. The post side surfaces are completely surrounded by the porous structure and the post outer surface is located at or below the porous structure outer surface.

Alternate aspects of this implant may include any of, or any combination of the following features: the posts have a circular cross section; there are three non-porous posts which may all be perpendicular to the non-porous body central axis; the non-porous body further comprises a constant diameter region and a tapering region, wherein there is at least two posts within the constant diameter region and at least two posts in the tapered region.

Yet another aspect of the invention is a prosthetic implant comprising a stem, a modular porous construct and a plurality of solid posts. The stem has first and second portions spaced along an axis. The first portion has a first diameter and the second portion has a second diameter, where the first diameter is larger than the second diameter. The modular porous construct is coupled to the first portion of the stem. The porous construct has a non-porous inner part and a porous outer part. The porous outer part may be formed on the non-porous inner part which defines an outer surface. The first portion of the stem has a plurality of solid posts that may be integrally formed with the non-porous inner part. The posts extend through the porous outer part. The posts have an outwardly facing surface forming part of the outer surface of the implant and side surfaces surrounded by the porous outer part.

Alternate aspects of the of the implant may include any of, or any combination of the following features: the porous outer part has a porous surface extending generally transverse to the axis facing the stem second portion; at least two posts extend through the porous surface in a direction parallel to the axis.

A method for attaching a tissue ingrowth surface to a stem during fabrication is disclosed. Here, a stem that has a solid outer portion is provided. An augment implant is fabricated that has a non-porous, axially extending inner portion which is covered by a porous outer portion. The porous outer portion defines an outer surface of the implant portion. The augment implant includes a plurality of solid posts integrally formed with the non-porous inner portion, which extend through the porous outer portion. The posts have an outwardly facing surface forming part of the implant portion outer surface. The outwardly facing surfaces of the solid posts are gripped with a tool and then press-fit onto the stem. During the press-fitting, a force is applied to the tool that grips the outwardly facing surfaces of the post.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
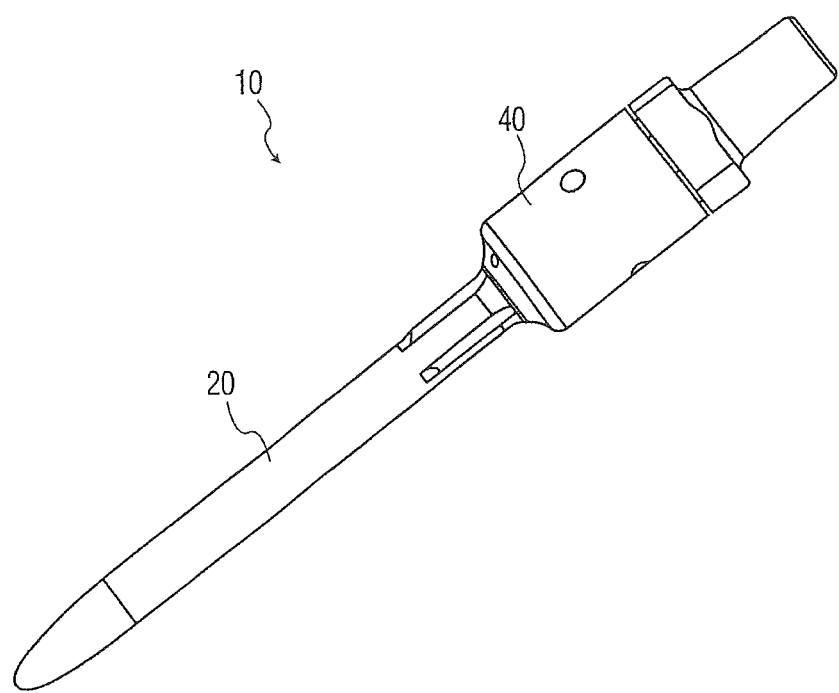
FIG. 1 is a perspective view of an assembled prosthetic implant comprising an assembled stem and an augment in accordance with one embodiment of the present invention.

Referring to FIG. 1, there is shown an embodiment of a prosthetic implant, generally denoted as 10, comprising a stem 20 and an augment 40. The augment 40, which is assembled with stem 20, and has a substantially porous outer surface. Implant 10 is designed for assembly to, for example, a joint component such as a prosthetic femoral component or tibial component.

Figure 2:
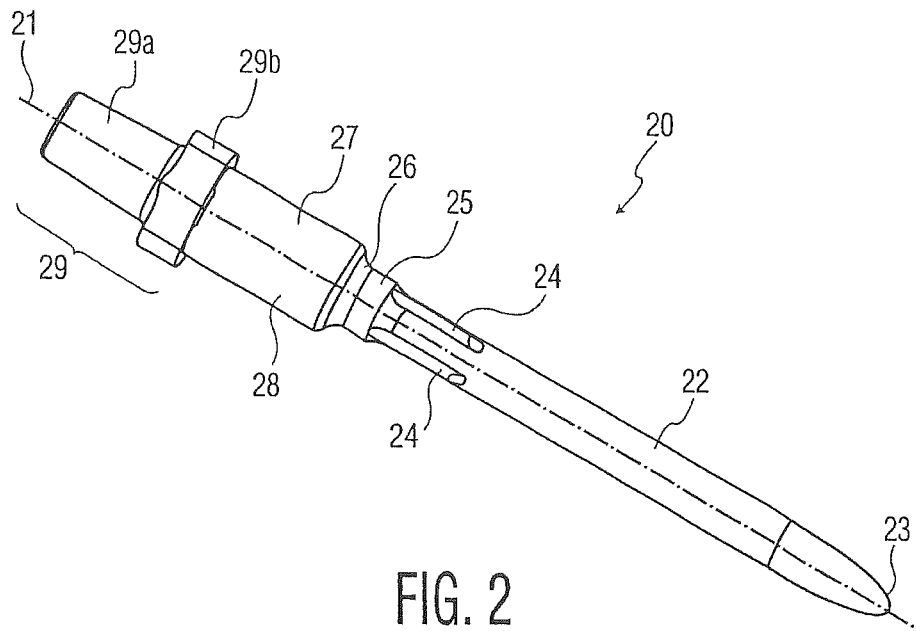
FIG. 2 is a perspective view of the stem shown in FIG. 1.

FIG. 2 illustrates one embodiment of a stem 20. Stem 20 is an elongate structure which extends circumferentially about a central axis 21 and may be manufactured from cobalt chrome, titanium or other implantable materials. Stem 20 may be used for either cemented or press-fit orthopedic applications. As is known in the art, stem 20 may have a small diameter region 22 that may taper towards a first end 23. Small diameter region 22 may include anti-rotation features 24 designed to resist rotational loads. Small diameter region 22 and first end 23 are the portions of stem 20 that would be implanted into the intramedullary canal of a long bone.

Stem 20 further comprises an intermediate constant diameter region 25, a large constant diameter region 27 and a transition region 26 connecting regions 25 and 27. There is an augment interface region 28 which comprises the outer surfaces of regions 25, 26 and 27. Stem 20 also includes a fixation region including a tapered engagement feature 29a and an anti-rotation feature 29b. The tapered engagement feature 29a is typically a Morse taper, but may be an alternate geometry. Engagement features 29a and 29b are designed to interface, by taper-locking or press-fitting, to an orthopedic implant such as a hip or knee implant.

Figure 3:
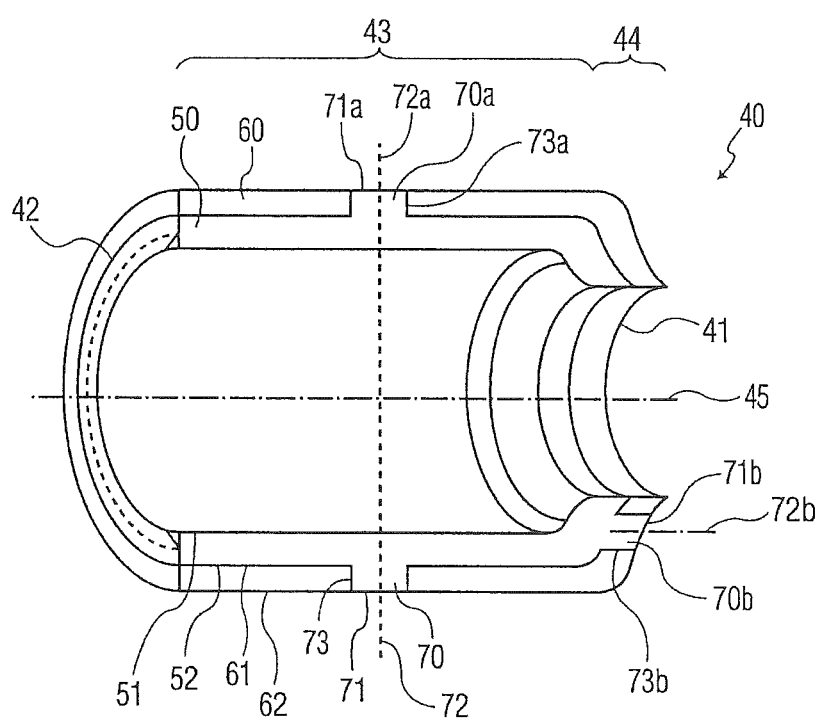
FIG. 3 is a perspective cross-sectional view of the augment shown in FIG. 1.
Figure 4:
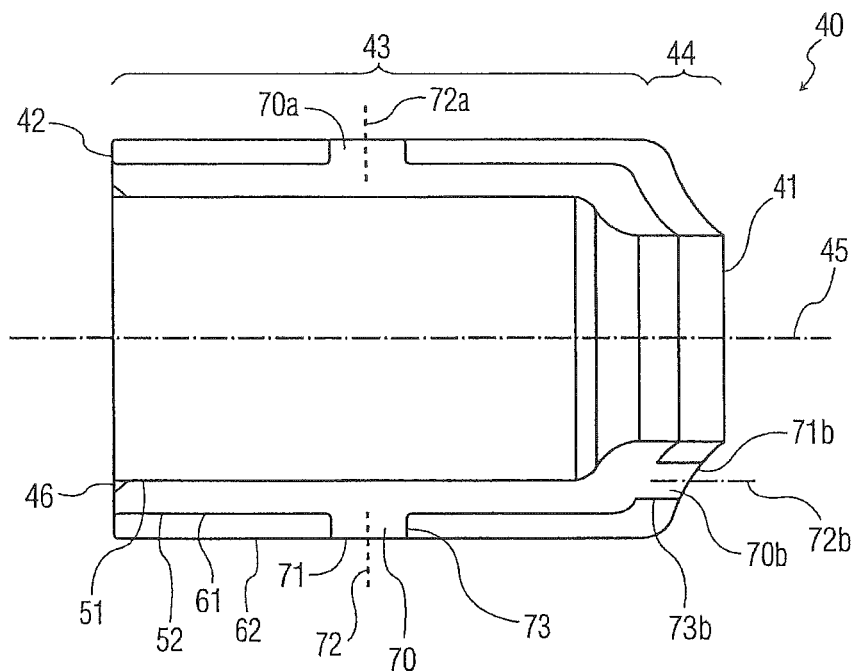
FIG. 4 is a side cross-sectional view of the augment shown in FIG. 3.

Referring to FIGS. 3 and 4, there is shown one embodiment of an augment 40. Augment 40 has a first end 41, a second end 42, a constant diameter region 43 and an inwardly tapered region 44. In this embodiment, augment 40 is a single structure that is manufactured from titanium material using the advanced machining techniques described in U.S. Pat. No. 7,537,664 and the U.S. Patent Application 2006/0147332. In alternate embodiments, the material may be PEEK, Cobalt Chrome, Polyethylene or other known implant materials. Although shown in cross-section, augment 40 is generally cylindrical extending circumferentially about a central axis 45.

Augment 40 is further comprised of a non-porous body 50, a porous structure 60 and a plurality of non-porous posts 70 which are described below. Non-porous, or solid, body 50 extends between an inner surface 51 and an outer surface 52. Solid body 50 has chamfer 46 extending about the inner surface 51 at second end 42. Porous structure 60 extends between an inner surface 61 and an outer surface 62, thereby defining a porous wall therebetween. As an example, a suitable porous ingrowth surface may have a porosity that ranges between 60-75%, with pore sizes ranging between 100-1000 microns. Porous structure 60 inner surface 61 is integrally formed on at least a portion of the solid outer surface 52. With relation to outer surface 52, outer surface 62 of porous structure 60 may be generally parallel, tapered, asymmetric or have a non-uniform geometry. The overall porosity of the porous structure 60 may be constant or variable between the inner surface 61, outer surface 62, first end 41 and second end 42.

A plurality of posts 70 are integrally formed on non-porous body 50 and extend from outer surface 52. Posts 70 have a central axis 72, an outer surface 73 that in a direction substantially parallel to the central axis 72, and an outwardly facing surface 71 that extends in a direction substantially perpendicular to central axis 72. In the embodiment shown, posts are cylindrical about central axis 72 and have a circular cross-sectional geometry, but it is understood that any geometry may be used. In alternate embodiments, outwardly facing surface 71 may be flat, arcuate or non perpendicular to central axis 72. In all embodiments, the outwardly facing surface 71 extends to a location at or below the porous structure outer surface 62. Outer surface 73 is surrounded by and integrally formed with porous structure 60. Further, posts 70 may be non-porous or porous. In embodiments where posts 70 are porous, the porosity of the posts 70 in this alternate embodiment would be less that the porosity of the porous structure 60.

Posts 70 may be located in the constant diameter region 43, inwardly tapered region 44, or both regions. There may be at least two posts 70 located within the constant diameter region 43. In this embodiment, the central axis 72 and 72a are aligned within the same cross-sectional plane 80. Further, the central axis 72 of posts 70, located within the constant diameter region 43, are substantially perpendicular to the augment central axis 45. In a preferred embodiment, there are three posts 70, within the constant diameter region 43, which are aligned within the same cross-sectional plane 80. In alternate embodiments, central axes 72 of posts 70 may not be aligned within the same cross-sectional plane and may be oriented non-perpendicular to the augment central axis 45. Yet in another alternate embodiment, post 70 may be a single ring-like structure extending circumferentially about central axis 45.

Further regarding posts 70, there may be at least one post 70b located within the inwardly tapered region 44 of augment 40. The posts 70b have a central axis 72b which is oriented substantially parallel to the augment central axis 45. Posts 70b are integrally formed with porous structure 60, and may be entirely or partially surrounded about outer surface 73b.

Referring to the embodiment in FIGS. 3 and 4, porous structure 60 extends between first end 41 and second end 42. Solid body 50 extends from second end 42, however, it does not extend to the first end 41. Therefore, porous structure 50 is located at the first end 41 and extends circumferentially about central axis 45. It is the intent of this embodiment to have the porous outer surface 62 extend from the constant diameter region and through the inwardly facing region 44. Having the porous structure 60 oriented in this manner will maximize contact with cortical bone once implanted within the patient, which will promote and optimize the quality of tissue ingrowth.

Figure 5:
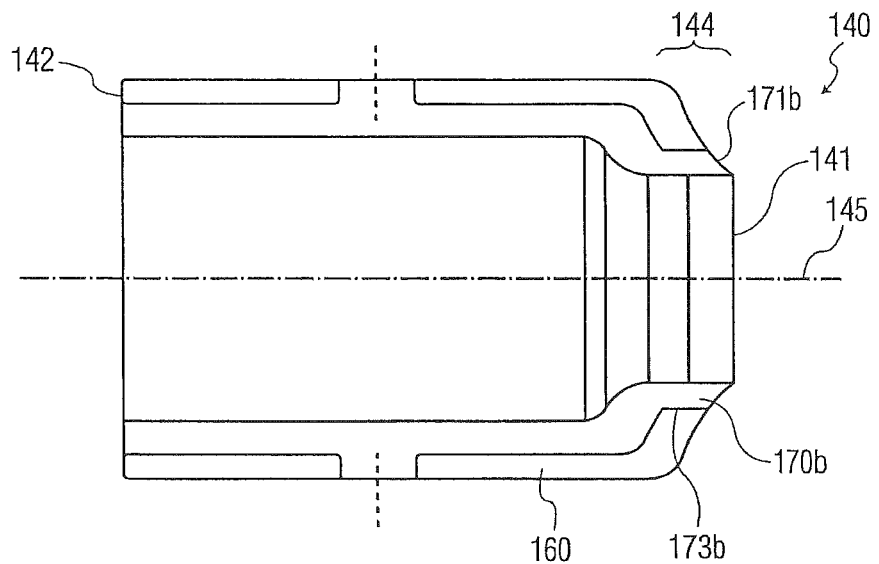
FIG. 5 is a side cross-sectional view of an alternate embodiment of an augment.

Referring to FIG. 5, an alternate embodiment of an augment 140 is shown. In this alternate embodiment, there is a single post 170b, in the form of a ring, located at first end 141 within the inwardly tapered region 144, which extends circumferentially about central axis 145. Outer surface 173b is partially surrounded by porous structure 160. It is noted that porous structure 160 extends from second end 142, but does not extend to first end 141. While the intent is also to promote and optimize the quality of tissue ingrowth as describe below, this embodiment may have advantages during implant assembly as will be described.

Figure 6:
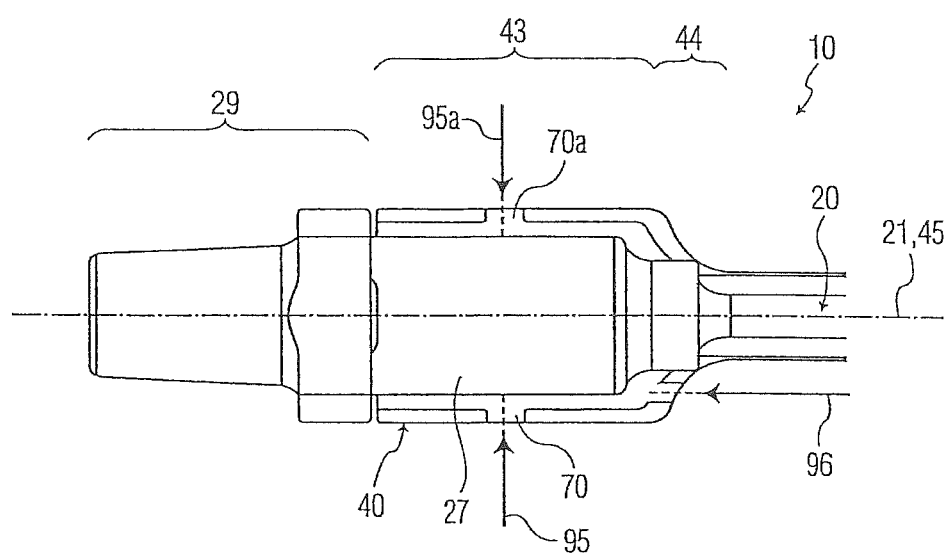
FIG. 6 is a cross-sectional side view of the assembled prosthetic implant, including assembly load indicator arrows.
Figure 7:
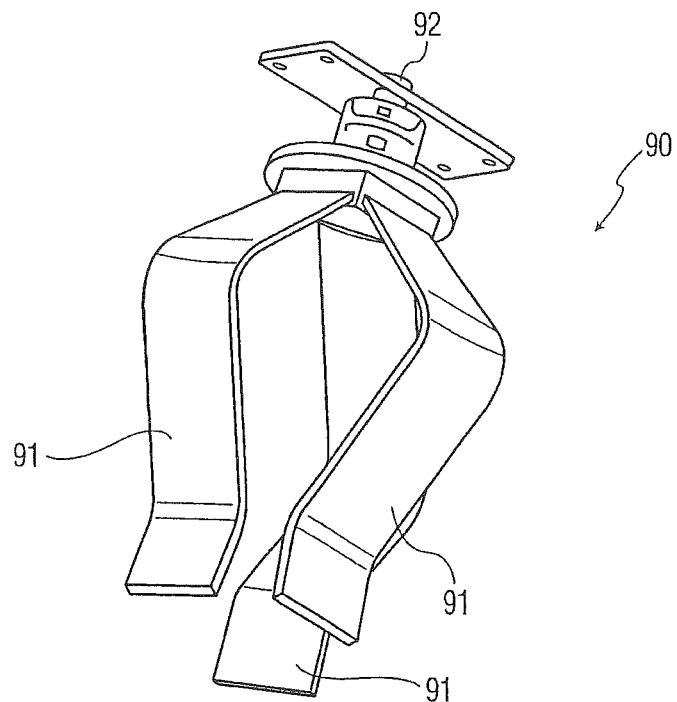
FIG. 7 is a perspective view of a tool used for assembly of the prosthetic stem and augment.

A method of fabricating a prosthetic implant 10 comprising a stem 20 and augment 40 is disclosed. FIG. 6 illustrates an implant 10 assembly and loading indicators used during assembly. A stem 20 and augment 40 are manufactured in accordance with the structures previously described. The stem 20 is stabilized by gripping at least a portion of fixation region 29 (not shown). Next, a tool grips the outwardly facing surfaces 71 of posts 70 in the constant diameter region 43 of augment 40. An example of this gripping tool 90 is illustrated in FIG. 7. The tool may be a known robotic claw with three gripping arms 91, and a first end 92 which would be connected to a robotic machine. In this example, each of the gripping arms 91 would engage one of three posts 70 within the constant diameter region 43. Here, first loads 95 are applied through the posts 70 which are substantially perpendicular to central axis 45. The augment is then moved so that central axis 45 is aligned with central axis 21 of stem 20.

After the axes are aligned, augment 40 is then advanced over the first end 23 and small diameter region 22 until the inner surface 51 at second end 42 of the augment 40 contacts the large constant diameter region 27 of the stem 20. Augment implant 40 is then advanced and press-fit onto the stem implant by applying a second load 96 through the posts 70 located within the inwardly tapered region 44. The second load 96 is applied in a direction substantially parallel to central axis 45. Second load 96 is sufficient to overcome a press-fit tolerance interference designed between the augment inner surface 51 and stem outer surface 28. Such tolerances are known to one skilled in the art. Augment 40 is advanced until the first end 41 is aligned with the intramedullary anti-rotation features 24, but does not contact the engagement feature 29b. Here, a tolerance gap remains between second end 42 and anti-rotation engagement feature 29b. This ensures a close fit at transition region 26. The resulting prosthetic implant 10 has an augment implant 40 press-fit onto a stem implant 20.

In an alternate embodiment of the method, the augment 40 shown in FIG. 5 is used. Here, there is a single ring-like post 170b located at first end 41 within the inwardly tapered region 44, which extends circumferentially about central axis 45. In this alternate embodiment, the longitudinal load is applied to the non-porous circumferential structure 70b.

In all methods described above, assembly tools interface with the augment 40 by gripping the post outwardly facing surfaces 71, and applying longitudinal loads to through the posts 70, 70b, 170b. The benefit of this assembly method is that loads may be applied to the augment 40 without damaging the porous structure 60.

Figure 8:
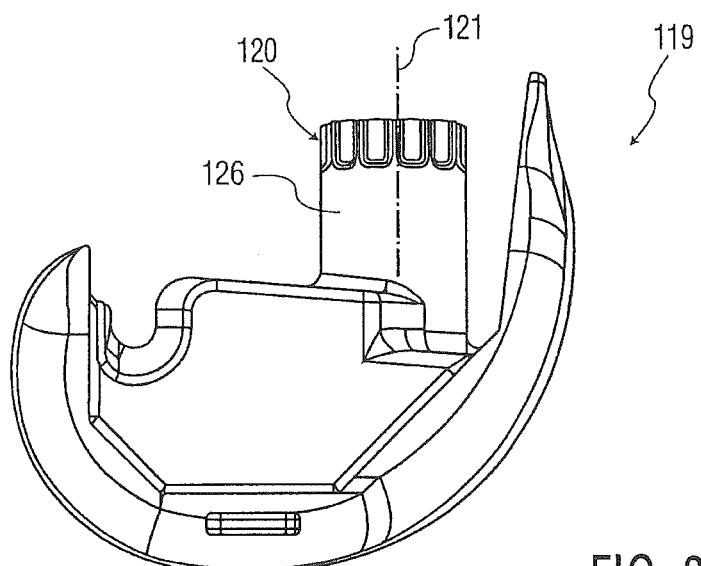
FIG. 8 is a perspective view of a femoral implant for use with the implant shown in FIG. 1 or FIG. 3.

FIG. 8 illustrates a femoral implant 119, which includes a boss element 120. Boss element 120 has a central axis 121 and represents an alternate embodiment of a stem implant. In this alternate embodiment boss element 120 has an outer surface 126 which extends circumferentially about the central axis 121. Outer surface 126 is designed to receive an augment 40 similar to that which has been described. Further, it is understood that the methods of assembly previously described may apply. While a femoral knee component is illustrated, it is understood that an augment may also be connected to a tibial knee implant, hip implant or any other articulating or non-articulating orthopedic implants used throughout the body.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for attaching a tissue ingrowth surface to a prosthetic femoral stem during fabrication comprising:
    obtaining a prosthetic femoral stem having first and second solid portions spaced along a longitudinal axis and respectively having first and second diameters, the first diameter larger than the second diameter;
    obtaining a modular augment having a first end, a second end, a constant diameter region, and an inwardly tapered region, said augment defined by:
        a non-porous solid body having a central axis, an inner surface and an outer surface, the inner surface extends circumferentially about the central axis and receives the stem first portion;
        a porous structure having an inner surface integrally formed on at least a portion of the non-porous body outer surface and having a tissue contacting outer surface, said tissue contacting outer surface defining a tissue ingrowth surface; and
        a plurality of non-porous solid posts integrally formed on the outer surface of the non-porous body as part of the non-porous body thereby forming a single structure; each of the non-porous posts having a flat outwardly facing surface, at least two posts are oriented perpendicular to the body central axis, the posts side surfaces are completely surrounded by the porous structure, the posts flat outwardly facing surfaces are not covered by the porous structure tissue contacting outer surface, the axis of at least two non-porous posts lying in a single plane perpendicular to the body central axis, wherein there is at least two non-porous posts within the constant diameter region;
    gripping the plurality of non-porous posts with a tool engaging the flat outwardly facing surfaces of the posts; and
    press-fitting the augment onto the first portion of the prosthetic femoral stem by applying a force to the tool gripping the outwardly facing surfaces of the non-porous posts.

2. The method as set forth in claim 1, wherein the posts have a circular cross section.

3. The method as set forth in claim 2, wherein there are three non-porous posts.

4. The method as set forth in claim 2, wherein there are three non-porous posts perpendicular to the central axis.

5. The method as set forth in claim 1, wherein there is at least two posts within the constant diameter region and at least two posts in the tapered region.

\* \* \* \* \*